United States Patent [19]

Bente, III et al.

[11] 4,293,415
[45] Oct. 6, 1981

[54] SILICA CHROMATOGRAPHIC COLUMN

[75] Inventors: Paul F. Bente, III, Landenberg, Pa.;
Ernest H. Zerenner, Newark;
Raymond D. Dandeneau,
Wilmington, both of Del.

[73] Assignee: Hewlett-Packard Company, Palo Alto, Calif.

[21] Appl. No.: 34,103

[22] Filed: Apr. 27, 1979

[51] Int. Cl.³ .............................................. B01D 15/08
[52] U.S. Cl. ................................... 210/198.2; 55/386; 65/DIG. 8
[58] Field of Search ....................... 55/386; 210/198.2; 65/3 A, 86

[56] References Cited

U.S. PATENT DOCUMENTS 3,116,161 12/1963 Purnell ............................... 55/386 X
3,977,854 8/1976 Fulmer et al. ........................ 65/3 R
4,043,905 8/1977 Novotny et al. ................ 210/198 C
4,155,733 5/1974 Sandbank et al. ....................... 65/86

FOREIGN PATENT DOCUMENTS 1955276 6/1972 Fed. Rep. of Germany ... 210/198 C

OTHER PUBLICATIONS

The Origination, Development and Potentialities of Glass Capillary Columns in Chromatography, vol. 8, No. 9, Sep. 1975, pp. 452-455.
The BaCO₃ Procedure for Preparation of Glass Capillary Columns: Further Information and Development by Grob et al. in Chromatography, vol. 10, No. 4, Apr. 1977, pp. 181–183.
Optical Transmission in Liquid Core Quartz Fibers by Stone in Applied Physics, Apr. 1972, pp. 78 and 79.
Construction of Long Lengths of Coiled Glass Capillary by Desty et al. in Analytical Chemistry, vol. 32, No. 2, Feb. 1960, pp. 302–304.

Primary Examiner—John Adee
Attorney, Agent, or Firm—Donald N. Timbie

[57] ABSTRACT

An open tubular or capillary chromatographic column made from drawn silica tubing having an exterior coating for protection from abrasion and moisture and means for holding it in a desired configuration.

23 Claims, 7 Drawing Figures

SUBSTANCES
1. PHENOL
2. O-CRESOL
3. 2,6-DIMETHYL PHENOL
4. m-CRESOL
5. 3,5-DIMETHYL PHENOL
6. 3,4-DIMETHYL PHENOL
7. 1-NAPHTHOL

SILICA CHROMATOGRAPHIC COLUMN

BACKGROUND OF THE INVENTION

This invention relates to improvements in capillary or open tubular columns that are used in gas chromatography to cause the constituents of sample material introduced at one end to emerge from the other end at different times.

Glass capillary chromatography columns, as they are used in the present state of the art, are formed by drawing a large diameter glass tube to form a straight stiff glass tube of the desired dimension, being typically 0.25 mm. inside diameter and 0.8 mm. outside diameter. The process is described in an article entitled "Construction of Long Lengths of Coiled Glass Capillary" at page 302 of the 1960 issue of *Analytical Chemistry*. After the glass column is drawn and has cooled, it is forced through a heated coiling tube which operates at a temperature above the annealing point of the glass and which serves to form the drawn tube into a coil being typically 10 to 15 centimeters in diameter, the tube being from 10 to 100 meters in length. The inside surface of these tubes is first etched with acid and then deactivated with a thin layer of suitable material so as to make it more inert for the particular sample material involved. This deactivating coating is then coated with a thin layer of stationary phase to form a column.

Glass capillary chromatography columns have several disadvantages in use, namely, that they are fragile and are easily broken if overstressed. Because they are relatively inflexible, the ends of the column must be straightened by heating them to the softening point in order to attach them to the injection port and detector fittings of a conventional gas chromatograph. Alternatively, transfer lines must be constructed to which the column can be connected and which are then connected to the injection port and detector fittings in the gas chromatograph.

A greater disadvantage of glass columns is that they distort peak shapes of sample materials that are as acidic as substituted phenols or as basic as aliphatic amines or otherwise reactive such as mercaptans, even if the surface is deactivated with organochlorosilicanes or with oxygenated polymers, such as poly(ethylene oxide) or polysiloxanes. This effect is caused by chemical activity of the glass surface, causing sample materials which are strongly acidic or basic or otherwise chemically reactive to adsorb strongly to the glass surface, causing these sample components not to elute from the column, or to elute with peak shapes seriously distorted from the usual symmetrical shape.

In an article entitled "The Origination, Development and Potentialities of Glass Capillary Columns" at page 452 of the September 1975 issue of *Chromatographia*, Vol. 8, No. 9, the possibility of silica capillaries is mentioned, but if columns of silica were made in the same way as glass columns, considerable difficulty would be encountered because the softening temperature of silica is much higher than the melting temperature of materials from which the coil forms are generally made. Furthermore, even if a column were made in this manner, softening the ends of the column so that they can be straightened as required to slide into the fittings of the instrument would require special heating means capable of producing high temperatures.

Furthermore, it has been reported that silica is not a suitable support for the stationary phase because silica catalyzes the breakdown of the macromolecules of the stationary phase and causes it to change slowly from a liquid to a quasisolid state. This is noted in an article entitled "The $BaCO_3$ Procedure for Preparation of Glass Capillary Columns: Further Information and Development" at page 181 of the publication *Chromatographia*, Vol. 10, No. 4, of April 1977.

BRIEF DISCUSSION OF THE INVENTION

One important aspect of this invention is the realization that silica capillary columns for gas chromatography could be made in much the same manner as hollow optical fibers, as described in an article entitled "Optical Transmissions in Liquid Core Quartz Fibers" at page 239 of the Apr. 11, 1972 issue of *Applied Physics Letters*, Vol. 20. Throughout this discussion, "silica" is intended to include $SiO_2$ in a glassy state, which may contain small amounts of sodium and potassium oxides but preferably does not contain substantial amounts of other oxides. On the other hand, the term "glass" or "glass columns" will be used to refer to the borosilicate or soda lime glass columns of the present state of the art. The term "stationary phase" is meant to include both partitioning materials as used in gas-liquid chromatography and reversibly adsorptive materials as used in gas-solid chromatography.

A large hollow tube of silica can be drawn to produce a column with an outside dimension that is small enough for it to be easily manipulated by hand, and a coating or coatings are immediately applied to the exterior surface so as to protect the silica tube from abrasion and moisture. Protection from abrasion is necessary because the slightest scratch can cause the tube to break when stressed, and protection from moisture is necessary because over a period of time moisture can weaken the surface of the tube until it breaks when stressed.

Because gas chromatography columns are used in controlled temperature ovens at temperatures which may be as high as 350° C. or higher, the protective coating on the outside is a material which is stable with respect to decomposition or oxidation at these temperatures. Materials such as polyimide or silicone rubber polymers or metals such as aluminum or nickel are suitable coatings. Protection from moisture can also be achieved by depositing a layer of silicon nitride ($Si_3N_4$) on the outside surface of the silica, but this coating is itself coated with a layer of polymer or metal to provide protection from abrasion.

Because tubing made in this manner is naturally straight, means are provided for holding it in a desired configuration so that it can be placed in the oven of a gas chromatograph. If, as is usual, the configuration is that of a coil, its form can be retained by tying wire or other material around it at a number of points.

A surprising characteristic of such silica columns, especially in view of the findings previously referred to, is that they provide a very good support for the stationary phase. Temperature stability of the stationary phase, as exhibited by the bleed rate, or the rate at which the stationary phase bleeds from the column when carrier gas is passing through it, is improved over that observed for borosilicate or soda lime glass capillary columns.

Of even greater importance, however, is the fact that when the usual deactivation procedures are applied to a silica surface, a much wider range of compounds can be chromatographed with substantially symmetrical peaks than is possible with glass columns, and in addition, it is possible to obtain excellent chromatograms for members of certain classes of compounds for which useful chromatograms cannot be attained with glass columns, e.g. phenols, free volatile fatty acids, mercaptans, and aliphatic amines.

THE DRAWINGS

Figure 1:
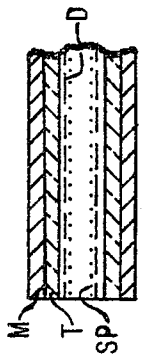
FIG. 1 is an axial cross-section of a portion of a chromatographic column in which a silica tube is coated on the outside with polyimide.
Figure 2:
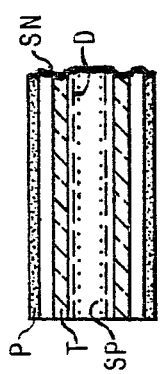
FIG. 2 is an axial cross-section of a portion of a chromatographic column in which a silica tube has a first coating of silicon nitride and a second coating of polyimide.
Figure 3:
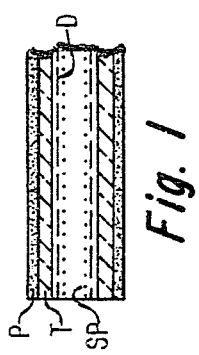
FIG. 3 is an axial cross-section of a portion of a chromatographic column in which a silica tube is coated with metal.

In FIGS. 1 through 3, the drawn silica tubing from which the column is made is indicated by T; the deactivation treatment, such as organochlorosilane or poly(ethylene oxide) that is applied to the inner surface of the tubing T is indicated by a dashed line D; and the stationary phase material that is applied to the deactivated surface is indicated by the dotted line SP.

The differences between the column portions illustrated in FIGS. 1 through 3 differ in the coating or coatings applied to the outer surface of the tube T to protect it from abrasion and also to some degree from moisture. In FIG. 1, a single coating P of polyimide is applied directly in the outer surface of the tube T. Polyimide is used as winding insulation for electrical motors and can withstand temperatures up to 350° C. Furthermore, it is flexible so that it does not crack when the tubing is bent or coiled.

The portion of the chromatographic column of FIG. 2 has a first coating SN of silicon nitride that has a high resistance to the penetration of moisture and an outer coating P of polyimide that has a high resistance to abrasion.

FIG. 3 illustrates a portion of a column having a metallic coating M directly on the outside of the tube T. Although any metal could be used, aluminum and nickel are preferred. It is also possible to use combinations of metal, e.g., copper could be applied directly to the silica tubing T as it is being drawn and electroless nickel could be deposited on the copper. The term "metallic coating" is intended also to cover metals protected by an oxide layer, as would be the case with aluminum.

The inner diameter of the silica tubes T is determined by chromatographic considerations and will generally be between 0.1 mm. and 0.4 mm. The outer diameter should be sufficiently small to provide the desired flexibility and consequent ruggedness without making the wall of the tube so thin that it will be crushed in use. Outer diameters between 0.15 mm. and 2.0 mm. have been found satisfactory. Polyimide coatings P having a thickness of approximately 0.05 mm. and silicon nitride coatings SN having a thickness of approximately 20 nanometers have been found satisfactory, but considerable latitude is permissible. A metal coating of approximately 0.025 mm. is useful. If the column is to be used at lower temperatures such as 250° C., a single coating of silicone rubber or the equivalent is satisfactory.

A highly satisfactory embodiment of the invention is a chromatrographic column consisting of silica tubing of 0.20 mm. inner diameter, 0.040 mm. wall thickness, coated on the outside with silicon nitride 20 nm coated with a polyimide layer 0.050 mm. thick. The inside of the tube is deactivated with poly(ethylene oxide) polymer treatment or with a chlorosilane treatment and coated with a 0.5 micron thick coating of methyl silicone stationary phase. The column length is between 10 and 100 meters.

In view of the fact that the silica columns of this invention are not annealed in the desired configuration, they do not retain their shape and some means must be provided for holding the column in place. Thus, for example, if the desired configuration is the customary coil shown in the oven of FIG. 4, it will be desirable to tie the various loops of the coil together by ties t.

Figure 4:
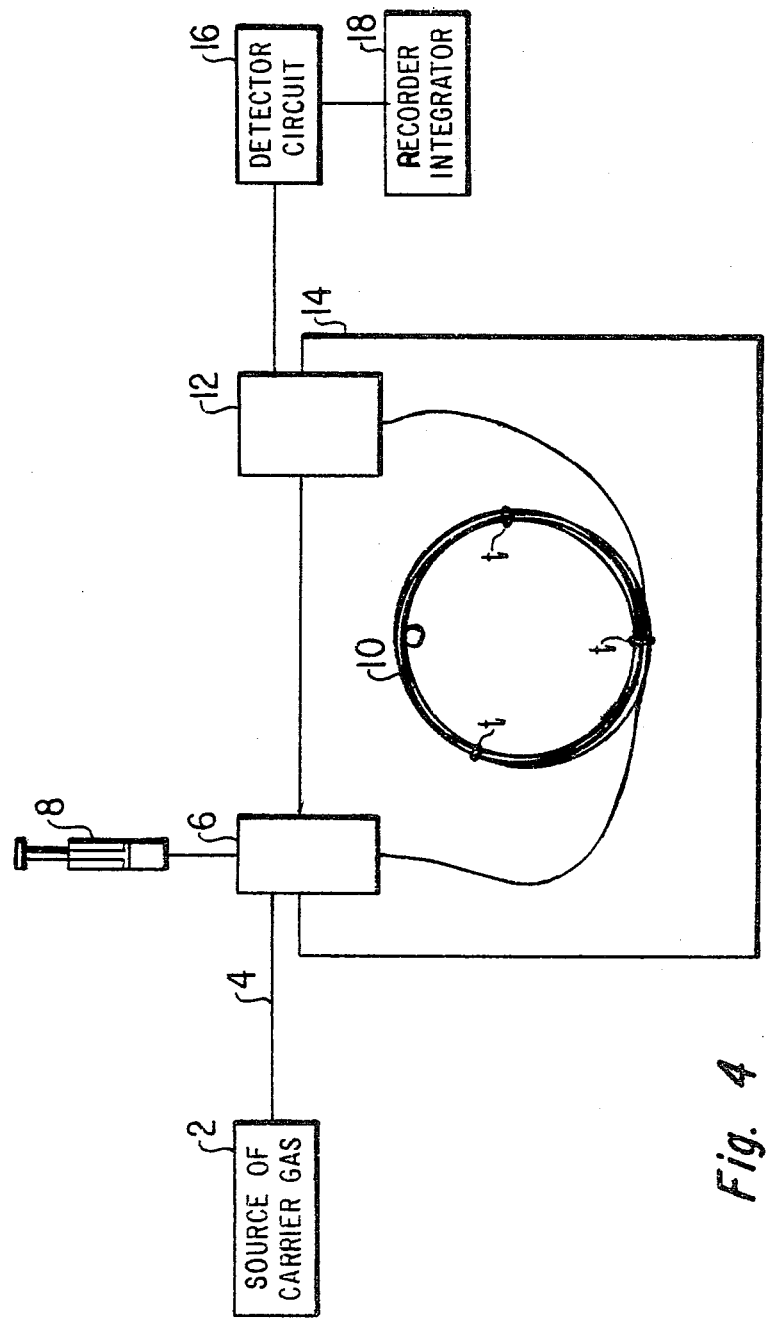
FIG. 4 is a schematic illustration of a chromatograph.

FIG. 4 schematically illustrates the basic elements of a chromatograph in which the columns of this invention may be used. For convenience, the actual dimensions have been distorted. A source 2 supplies carrier gas through a tube 4 to the injection port 6. A small volume of sample is introduced into the carrier gas stream by a syringe 8 acting through the injection port 6. A fraction of the carrier gas stream carries the sample into the flexible silica column 10 of this invention. The downstream end of the column is connected to a detector 12 where the eluting constituents are sensed. The injection port 6, the column 10, and the detector 12 are mounted in a controlled temperature oven 14. The detector signal is processed by a detector circuit 16 and the resulting chromatogram is displayed on a recorder and integrator 18.

Figure 5:
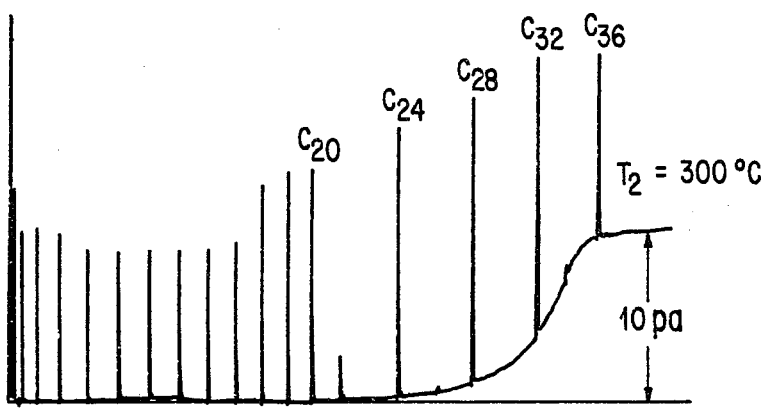
FIG. 5 illustrates the temperature stability obtained with a silica column.

FIG. 5 is a temperature programmed chromatogram of a series of n-hydrocarbons on a flexible silica column deactivated with a poly(ethylene oxide) carbowax 20M ® and coated with a poly(methyl siloxane) SP-2100 stationary phase. A stationary phase bleed signal of 10 picoamperes at 300° C. was observed with a flame ionization detector. This shows temperature limit of the stationary phase significantly higher than that of 270° C. observed for conventional glass capillary columns.

Figure 6:
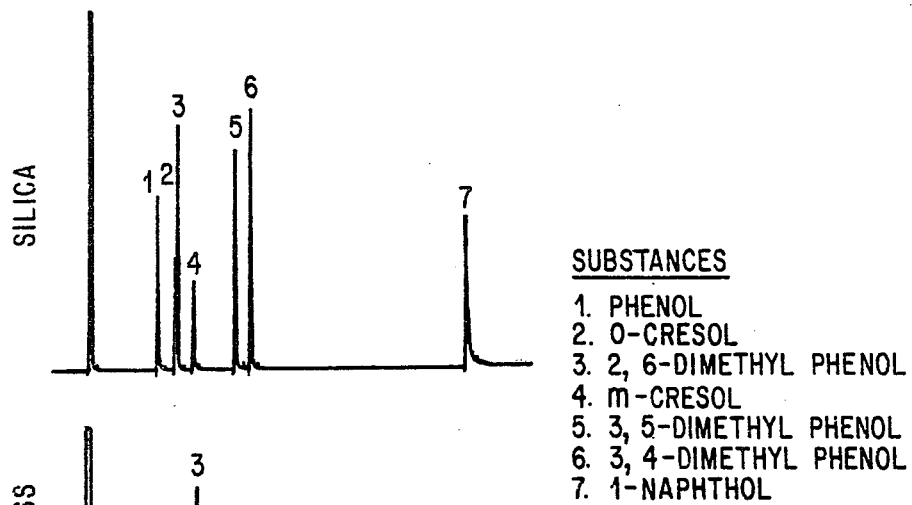
FIG. 6 is a comparison for chromatograms of phenols obtained with silica and glass columns.

FIG. 6 is a comparison of chromatograms of a series of phenols which are identified as peaks 1 through 7 obtained on a conventional column of soda lime glass and a flexible silica column. The stationary phase for both columns was poly(methyl siloxane) SP-2100. The instrument conditions for both chromatograms were as follows: temperature 1, 100° C.; time 1, 2 minutes; rate, 10° C./minute; temperature 2, 190° C.; time 2, 5 minutes; injection temperature, 250° C.; detector temperature, 250° C. Note the severe tailing of peaks in soda lime column chromatogram and the significantly improved peak shapes in the silica column chromatogram.

Figure 7:
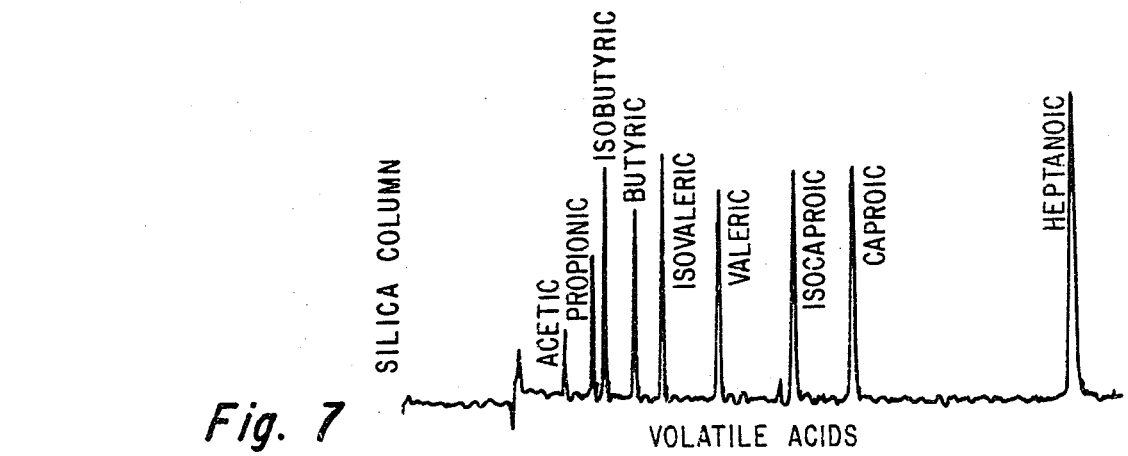
FIG. 7 is a chromatogram of free volatile fatty acids obtained with a silica column.

FIG. 7 is a chromatrogram of a sample of free volatile fatty acids in water solution from a flexible silica column of 0.21 mm. inner diameter deactivated with a thermal poly(ethylene oxide) carbowax 20M procedure and coated with a stationary phase of poly(ethylene oxide) carbowax 20M. The column temperature was 140° C. Sample components were approximately 100 picograms each. The symmetrical peaks for such small sample quantities indicate no sample adsorption is occurring for these reactive compounds. As far as applicants are aware, such results cannot be attained with glass columns.

It will also be recognized by one skilled in the art of chromatography that the flexible silica material described for use as capillary columns is also well suited for use as a transfer tube. Such a transfer line is used to transport sample constituents from a separating column to a detector which is located so that the column cannot conveniently be connected to it, as is the case when a separate instrument such as a mass spectrometer or infrared or ultraviolet spectrometer is used as a detector, or when multiple detectors are used and the effluent from the column is divided or split and conveyed to these multiple detectors in parallel. Transfer lines are also used to carry fluid samples from a remote sampling site to the sample injector, as would be the case with a system for sampling air or a liquid stream at various points.

Transfer lines differ from separating columns in that transfer lines contain no stationary phase so that they effect no separation of sample components, but may be deactivated so that they convey the stream unchanged in composition.

The chemical inertness, flexibility and ruggedness of a transfer made from silica in the same manner as the abovedescribed capillary columns would be useful and advantageous.

What is claimed is:

1. A chromatographic column for separating components of sample material flowing through it, comprising
   a hollow tube of drawn silica of thin wall construction with a high degree of flexibility,
   the inner surface of said tube being coated with a stationary phase material and there being an unobstructed passage along the axis of the tube, and
   a coating formed on the outer surface of the tube as it is drawn for protecting the said outer surface from abrasion and moisture.

2. A chromatrographic column as set forth in claim 1 wherein the column has the configuration of a coil.

3. a chromatographic column as set forth in claim 1 wherein a deactivation treatment is applied to the inner surface of the tube before the stationary phase is applied.

4. A chromatographic column as set forth in claim 3 wherein said deactivation process is a treatment of the surface with an organochlorosilane.

5. A chromatorgraphic column as set forth in claim 3 wherein said deactivation process is a treatment of the surface with poly(ethylene oxide).

6. A chromatographic column as set forth in claim 3 wherein said deactivation process is a treatment of the surface with dimethyldichlorosilane.

7. A chromatographic column as set forth in claim 3 wherein said deactivation process is a treatment of the surface with trimethylchlorosilane.

8. A chromatographic column as set forth in claim 3 wherein said deactivation process is a treatment of the surface with hexamethyldisilazane.

9. A chromatographic column as set forth in claim 1 wherein said coating on the outside of said tube is comprised of polyimide.

10. A chromatographic column as set forth in claim 1 wherein said coating on the outside of said tube is comprised of silicone rubber.

11. A chromatographic column as set forth in claim 1 wherein said coating on the outside of said tube is comprised of a first layer of silicon nitride and a second layer of polyimide.

12. A chromatographic column as set forth in claim 1 wherein said coating on the outside of said tube is comprised of a first layer of silicon nitride and a second layer of silicone rubber.

13. A chromatographic column as set forth in claim 1 wherein said coating on the outside of said tube is comprised of metal.

14. A capillary chromatographic column, comprising
    a hollow tube of drawn silica,
    the inner surface of said tube having been deactivated,
    a coating of stationary phase material on said deactivated inner surface, there being an unobstructed passage along the axis of the tube, and
    a coating formed on the outer surface of the tube for protecting it from abrasion and moisture so that it is sufficiently flexible to be easily formed by hand into a coil having a diameter of 10 centimeters.

15. A chromatographic column as set forth in claim 14 wherein said coating on the outside of said tube is comprised of polyimide.

16. A chromatographic column as set forth in claim 14 wherein said coating on the outside of said tube is comprised of silicone rubber.

17. A chromatographic column as set forth in claim 14 wherein said coating on the outside of said tube is comprised of a first layer of silicon nitride and a second layer of polyimide.

18. A chromatographic column as set forth in claim 14 wherein said coating on the outside of said tube is comprised of a first layer of silicon nitride and a second layer of silicone rubber.

19. A chromatographic column as set forth in claim 14 wherein said coating on the outside of said tube is comprised of metal.

20. Tubing for a capillary chromatographic column, comprising
    a hollow tube of drawn quartz,
    stationary phase material coated along the inner surface of said tube, there being an unobstructed passageway along the axis of said tube,
    a coating formed on the outside surface of said tube as it is drawn that protects said outside surface from moisture and abrasion,
    the inner diameter of said tube being such as to provide desired chromatographic performance, and
    the outer diameter of said tube being less than 2.0 millimeters by an amount providing a wall thickness that permits coiling the tube by hand into a coil having a diameter of 15 centimeters.

21. A capillary chromatographic column comprising
    a hollow tube of drawn silica having an inner diameter within the range of 0.1 mm to 0.4 mm and an outer diameter within the range of 0.15 mm to 1.0 mm,
    the inner surface of said tube being coated with a stationary phase, and
    the outer surface of said tube having a coating formed thereon for protecting it from abrasion and moisture, whereby the column can be formed by hand into a coil having a diameter of 10 centimeters.

22. A capillary column as set forth in claim 21 wherein said inner surface has been deactivated prior to the formation of the stationary phase thereon.

23. A capillary column as set forth in claim 21 wherein the coating on the outside surface of the tube is polyimide.

* * * * *